United States Patent [19]

Jolly

[11] Patent Number: Plant 6,560

[45] Date of Patent: Jan. 24, 1989

[54] MINIATURE ROSE PLANT NAMED 'SWINGER'

[76] Inventor: Nelson F. Jolly, P.O. Box 188 Gregg Neck Rd., Galena, Md. 21635

[21] Appl. No.: 32,432

[22] Filed: Mar. 30, 1987

[51] Int. Cl.[4] ..... A01H 5/00

[52] U.S. Cl. ..... Plt./7

[58] Field of Search ..... Plt./7

*Primary Examiner*—James R. Feyrer

[57] ABSTRACT

A new and distinct variety of rose plant of the miniature rose class, which was originated by my crossing Rise n Shine as seed parent and Puppy Love as pollen parent; characterized by a strong growing upright winter-hardy plant producing medium golden yellow buds which open to a bright yellow flower and finishes to a golden ivory before fading.

1 Drawing Sheet

The present invention relates to a new and distinct variety of rose plant of the miniature rose class, which was originated by my crossing as seed parent the rose known as "Rise n Shine" (U.S. Plant Pat. No. 4,231) and the rose known as "Puppy Love" (U.S. Plant Pat. No. 4,292) as pollen parent.

Among the novel characteristics possessed by this new variety which distinguished it from all other varieties of which I am aware are:

1. Well-formed blooms of medium-yellow coloring with ivory high-lights on velvety petals are borne primarily one to a stem on strong erect individual stems.

2. A strong, upright growing plant with much branching and excellent contrasting yellow-green foliage.

3. Produces attractive rose hips in late fall, not only lending additional color to the plant, but also mixing it useful as a seed parent.

Asexual reproduction by budding of the new variety as performed in Kent County, Md. shows that the foregoing and other distinguishing characteristics come true to form and are established and transmitted through succeeding propagation.

The new and improved rose variety which I have developed is an unusually well-formed medium to light yellow miniature rose with excellent flower and bud form and performs very well in planters and hanging baskets. The ivory highlights of each petal makes the plant very showy wherever a light, crisp color is useful in the garden or pot or terrace. The uniform coloration lasts well outdoors and maintains its color until the petals drop.

The accompanying drawing shows typical specimens of the vegetative growth and flowers of the new variety named "Swinger" (Jolswi), in different stages of development and as depicted in color as nearly true as it is reasonably possible to make the same in a color illustration of this character.

The following is a detailed description of my new variety, with color terminology in accordance with The Royal Horticultural Society Colour Chart (R.H.S.C.C.). The terminology used in color description herein refers to plate numbers in the aforementioned color chart, e.g., "13-B" is plate 13-B of The Royal Horticultural Society Colour Chart.

Parentage: Seedling.

*Seed parent.*—"Rise n Shine".

*Pollen parent.*—"Puppy Love".

Class: Miniature.

The following observations are made of specimens grown outdoors at Kent County, Md., during the month of July.

FLOWER

Blooming habit: Continuous.

A. Bud:

(1) *Size.*—Medium.

(2) *Form.*—Excellent, high-centered.

(3) *Color.*—When sepals first divide: a golden medium yellow 13-B forms the basic coloration as the individual bloom opens with a fading to 13-C and 13-D as the flower expands and opens to a golden ivory tonality.

(4) *Sepals.*—Heavy, extending slightly beyond bud.

(5) *Peduncle.*—Length 4½ cm. Aspect—Straight. Strength—medium. Color.—144-C.

B. Bloom:

(1) *Size.*—1¾".

(2) *Borne.*—Singly.

(3) *Form.*—High centered, becoming recurled at finish.

(4) *Petalage.*—32–34.

(5) *Color.*—During first two days. Center of Flower—near 12-C. Outer petals—near 13-C. Base of petals: 12-B. Reverse of petals—near 13-C.

(6) *Color change.*—General tonality from a distance is a light golden yellow with ivory finish with tones near 19D to 27D. Color lightens as bloom ages.

C. Petals:

(1) *Texture.*—Medium.

(2) *Appearance.*—Satiny.

(3) *Form.—Teardrop, edges rolled.*

(4) *Arrangement.*—Regularly arranged shingle-like overlay.

(5) *Petaloids in center.*—Few.

(6) *Persistence.*—Persist.

(7) *Fragrance.*—Slight.

(8) *Lasting quality.*—5–7 days on plant, 3–5 days as cut flower.

REPRODUCTIVE ORGANS

A. Stamens, anthers: Irregularly arranged around styles.
(1) *Color.*—Yellow-orange, near to 14-A.
B. Pollen: Color is yellow-orange, near to 14-C.
C. Styles: Medium.
D. Stigmas:
*Color.*—Yellow-orange — 14-C.
E. Hips: Globular and abundant, near 168-C, seeds protrude slightly.

PLANT

A. Form: Spreading and upright.
B. Growth: Very vigorous.
*Height attained.*—65–70 cm.
C. Foliage: Compound of 5 leaflets.
(1) *Size.*—Small.
(2) *Quantity.*—Abundant.
(3) *Color.*—New foliage: upper side — 147-B, under side — 59-B. Old foliage: upper side — 137-C, under side — 138-C.
(4) *Shape.*—Oval, pointed.
(5) *Texture.*—Upper side — smooth. Under side — rough.
(6) *Edge.*—Serrated.
(7) *Serration.*—6 per cm.

(8) *Leaf stem.*—Color — 146-D; under side — 152-A.
(9) *Stipules.*—Medium, slightly bearded.
D. Wood:
(1) *New wood.*—Color — 146-A. Bark — smooth.
(2) *Old wood.*—Color — 144-A. Bark — smooth.
E. Thorns:
(1) *Thorns.*—Quantity: on main stalks from base — ordinary; on laterals from stalk — ordinary. Form: flat base, slightly hooked. Length: medium. Color when young — 178-A. Position: irregular.
(2) *Prickles.*—Quantity: On main stalks — none; on laterals — none.
F. Plant's disease resistance:
(1) *Mildew.*—Moderate.
(2) *Blackspot.*—Moderate.
(3) *Rust.*—None observed.
G. Winter hardiness: Very winter hardy.

I claim:

1. A new and distinct variety of rose plant of the miniature rose class, substantially as shown and described, characterized particularly by flowers of unusually brilliant golden yellow opening to a clear golden ivory flower with deeper yellow tones at base of inner petal; flower form is excellent on this vigorous, upright growing plant.

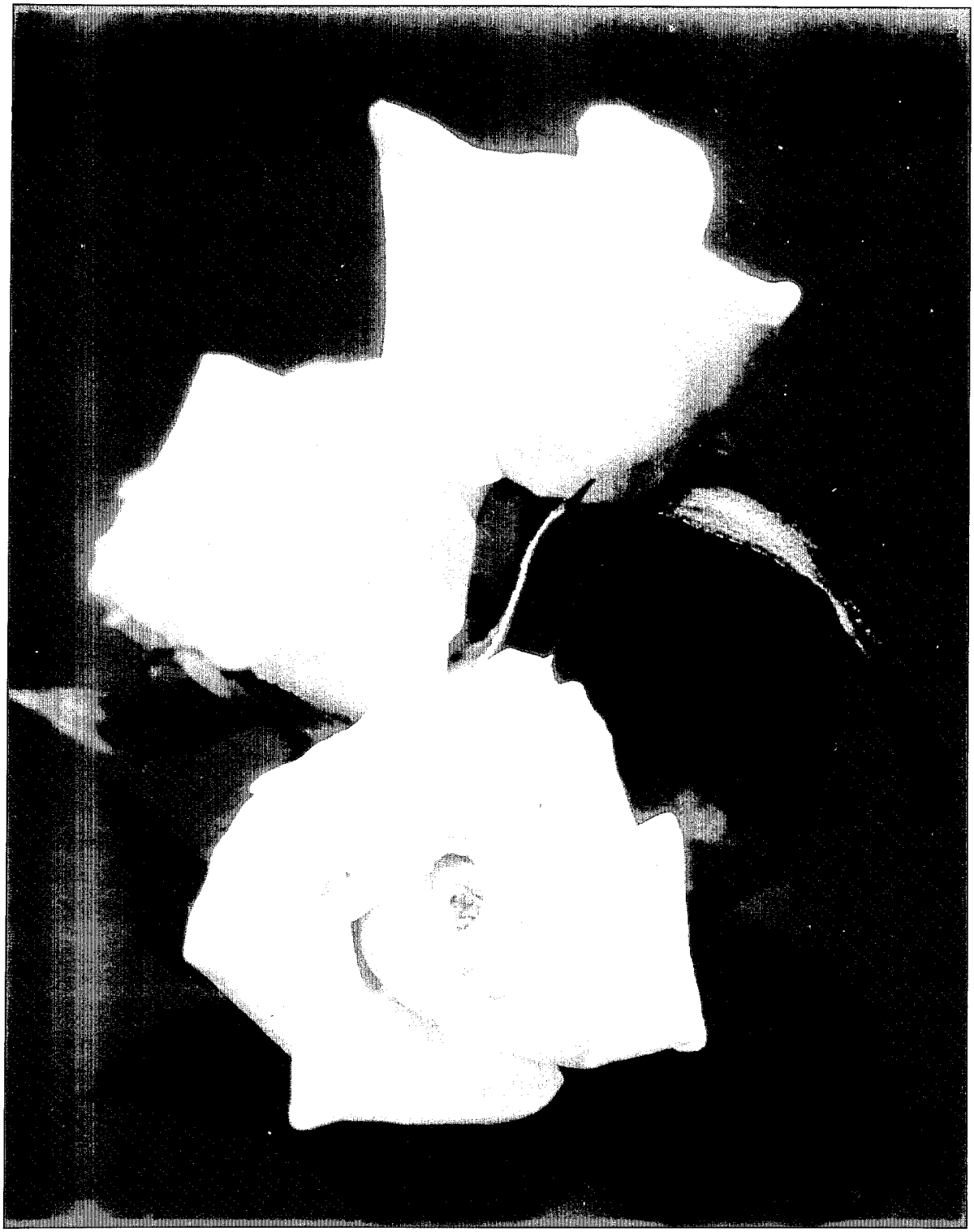

* * * * *